United States Patent
Dunlop

(10) Patent No.: US 9,446,212 B2
(45) Date of Patent: Sep. 20, 2016

(54) METHOD AND APPARATUS FOR DELIVERING A FLUID TO A PATIENT

(76) Inventor: Colin Dunlop, East Ryde (AU)

(*) Notice: Subject to any disclaimer, the term of this patent is extended or adjusted under 35 U.S.C. 154(b) by 840 days.

(21) Appl. No.: 13/388,914

(22) PCT Filed: Aug. 3, 2010

(86) PCT No.: PCT/AU2010/000975
§ 371 (c)(1),
(2), (4) Date: Apr. 23, 2012

(87) PCT Pub. No.: WO2011/014908
PCT Pub. Date: Feb. 10, 2011

(65) Prior Publication Data
US 2012/0216807 A1 Aug. 30, 2012

(30) Foreign Application Priority Data
Aug. 3, 2009 (AU) .................. 2009903614

(51) Int. Cl.
*A61M 16/01* (2006.01)
*A61M 16/06* (2006.01)
(Continued)

(52) U.S. Cl.
CPC .............. *A61M 16/01* (2013.01); *A61D 7/04* (2013.01); *A61M 16/0009* (2014.02);
(Continued)

(58) Field of Classification Search
CPC .. A61M 16/06; A61M 16/08; A61M 16/202; A61M 16/104; A61M 16/105; A61M 16/1015; A61M 16/085; A61M 16/1055; A61M 16/0666; A61M 16/009; A61M 15/00; A61M 16/00; A61M 16/10; A01K 1/031; A01K 1/00; A01K 1/02; A01K 1/03; A01K 1/06; A01K 1/0613; A01K 13/00; A01K 13/001; A22B 3/00; A22B 3/005; A61B 5/08; A61D 7/00; A61D 7/04; A62B 19/00; F16L 55/04
USPC ............ 128/203.12, 203.15, 204.18, 200.14, 128/200.19, 203.29, 205.25, 910, 200.11, 128/202.27, 204.14, 912, 911, 202.23, 128/203.28, 206.24; 119/420, 52.1, 416, 119/417, 418, 419
See application file for complete search history.

(56) References Cited

U.S. PATENT DOCUMENTS 2,960,985 A 11/1960 Wiese
3,556,097 A * 1/1971 Wallace .................. 128/202.23
(Continued)

FOREIGN PATENT DOCUMENTS

AU 20090903614 8/2009
DE 202006013064 U1 1/2007
(Continued)

OTHER PUBLICATIONS

International Search Report issued on Nov. 29, 2010 for application PCT/AU2010/000975, filed on Aug. 3, 2010 and published as WO 2011/014908 on Feb. 2, 2011 (Applicant/Inventor—Dunlop) (6 pages).
(Continued)

*Primary Examiner* — Annette Dixon
(74) *Attorney, Agent, or Firm* — Ballard Spahr LLP

(57) ABSTRACT

An apparatus for facilitating delivery of a fluid, such as an anaesthetic fluid, to the respiratory tract of a subject. It includes a fluid line substrate, in the form of a block having conduits formed therein for delivery and removal of an anaesthetic. A subject port is formed to receive the anatomy of the patient. A mask apparatus is arranged for mating with the subject port, and having an opening to receive the nose and mouth of the subject.

32 Claims, 10 Drawing Sheets

(51) Int. Cl.
  *A61D 7/04*    (2006.01)
  *A61M 16/18*   (2006.01)
  *A61M 16/00*   (2006.01)
  A61M 16/08    (2006.01)
  A61M 16/10    (2006.01)

(52) U.S. Cl.
  CPC ......... *A61M 16/186* (2013.01); *A61M 16/009* (2013.01); *A61M 16/06* (2013.01); *A61M 16/0816* (2013.01); *A61M 16/0875* (2013.01); *A61M 16/104* (2013.01); *A61M 2205/3368* (2013.01); *A61M 2205/3653* (2013.01); *A61M 2205/84* (2013.01); *A61M 2230/435* (2013.01)

(56) References Cited

U.S. PATENT DOCUMENTS

| | | | | |
|---|---|---|---|---|
| 3,713,440 | A * | 1/1973 | Nicholes | 128/205.12 |
| 3,814,091 | A * | 6/1974 | Henkin | 128/202.22 |
| 3,901,230 | A * | 8/1975 | Henkin | 128/205.17 |
| 3,960,148 | A * | 6/1976 | Dryden | 128/203.16 |
| 4,051,847 | A * | 10/1977 | Henkin | 128/202.22 |
| 4,248,218 | A * | 2/1981 | Fischer | 128/204.18 |
| 4,265,239 | A * | 5/1981 | Fischer et al. | 128/205.17 |
| 4,332,244 | A | 6/1982 | Levy et al. | |
| 4,520,808 | A * | 6/1985 | LaBauve | 128/200.14 |
| 4,582,055 | A * | 4/1986 | McDougal et al. | 128/202.12 |
| 4,721,060 | A * | 1/1988 | Cannon et al. | 119/420 |
| 4,794,921 | A * | 1/1989 | Lindkvist | 128/203.29 |
| 4,807,617 | A * | 2/1989 | Nesti | 128/205.12 |
| 4,860,741 | A * | 8/1989 | Bernstein et al. | 128/204.18 |
| 5,297,502 | A * | 3/1994 | Jaeger | 119/420 |
| 6,776,158 | B1 * | 8/2004 | Anderson et al. | 128/203.12 |
| 6,948,493 | B2 * | 9/2005 | Dunlop | 128/203.12 |
| 7,004,162 | B1 | 2/2006 | Foley et al. | |
| 7,406,966 | B2 | 8/2008 | Wondka | |
| 7,461,652 | B2 * | 12/2008 | Dalgetty et al. | 128/203.15 |
| 7,464,707 | B2 * | 12/2008 | Dalgetty et al. | 128/203.15 |
| 7,503,323 | B2 * | 3/2009 | Dalgetty et al. | 128/203.15 |

FOREIGN PATENT DOCUMENTS

| | | |
|---|---|---|
| EP | 2174617 A1 | 4/2010 |
| EP | 10805873.6 | 8/2010 |
| WO | WO-2008/070918 A1 | 6/2008 |
| WO | PCT/AU2010/000975 | 8/2010 |

OTHER PUBLICATIONS

Written Opinion issued on Nov. 19, 2010 for application PCT/AU2010/000975, filed on Aug. 3, 2010 and published as WO 2011/014908 on Feb. 2, 2011 (Applicant/Inventor—Dunlop) (10 pages).

International Preliminary Report on Patentability issued on Nov. 21, 2011 for application PCT/AU2010/000975, filed on Aug. 3, 2010 and published as WO 2011/014908 on Feb. 2, 2011 (Applicant/Inventor—Dunlop) (19 pages).

Extended European Search Report issued on Jun. 30, 2014 for application EP 10805873.6, filed on Aug. 3, 2010 and published as EP 2461861 on Jun. 13, 2012 (Applicant/Inventor—Dunlop) (11 pages).

* cited by examiner

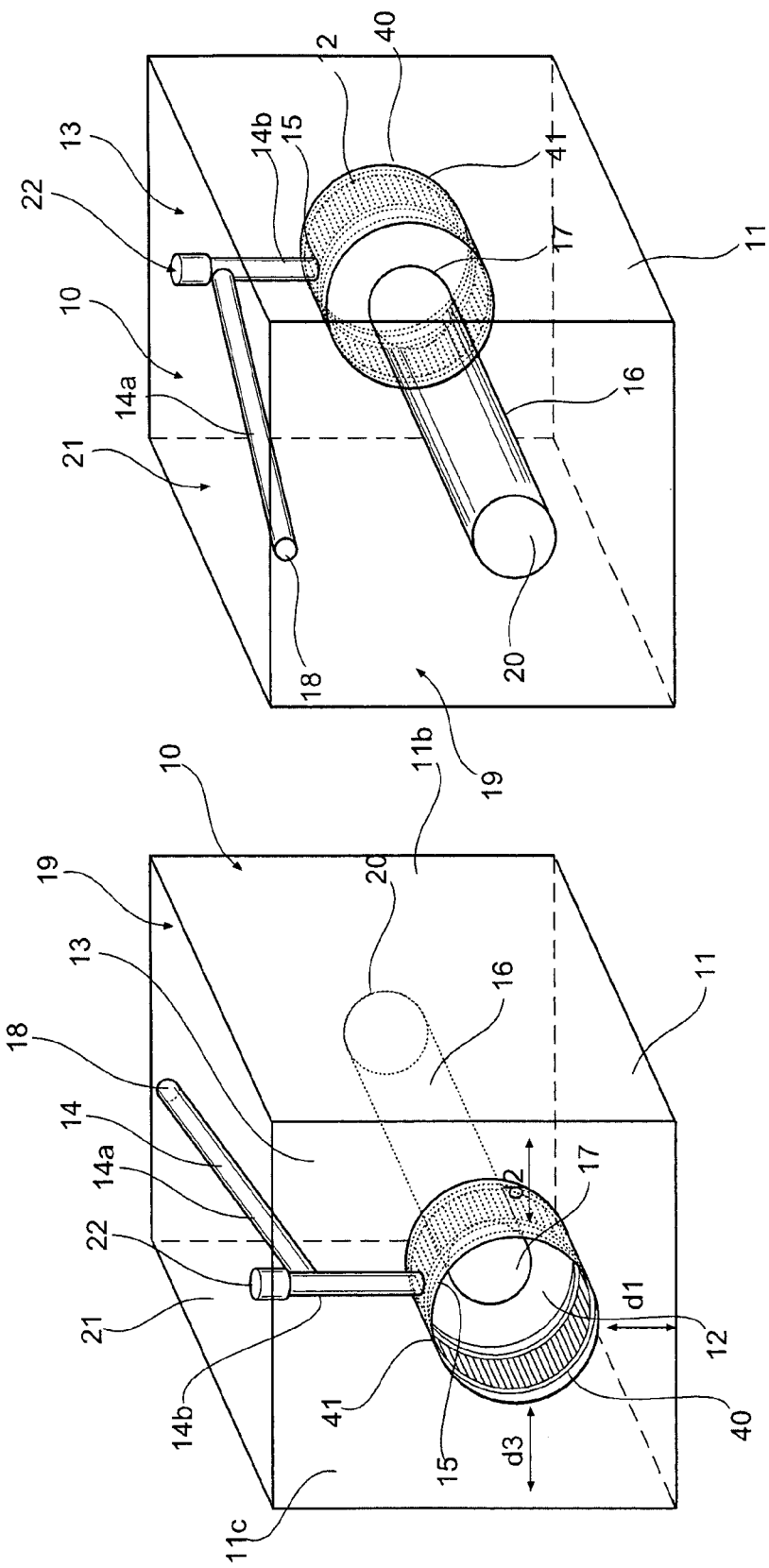

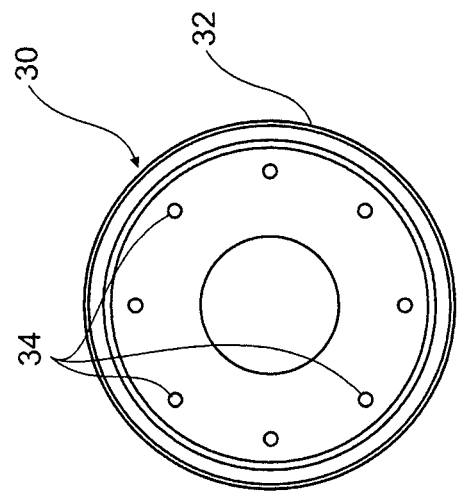
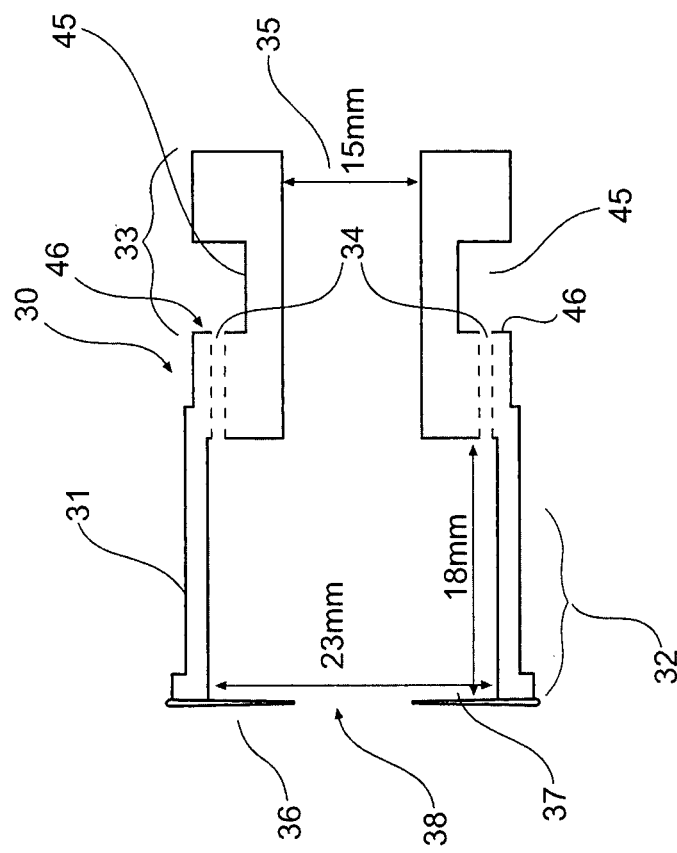
Fig 6
Fig 5

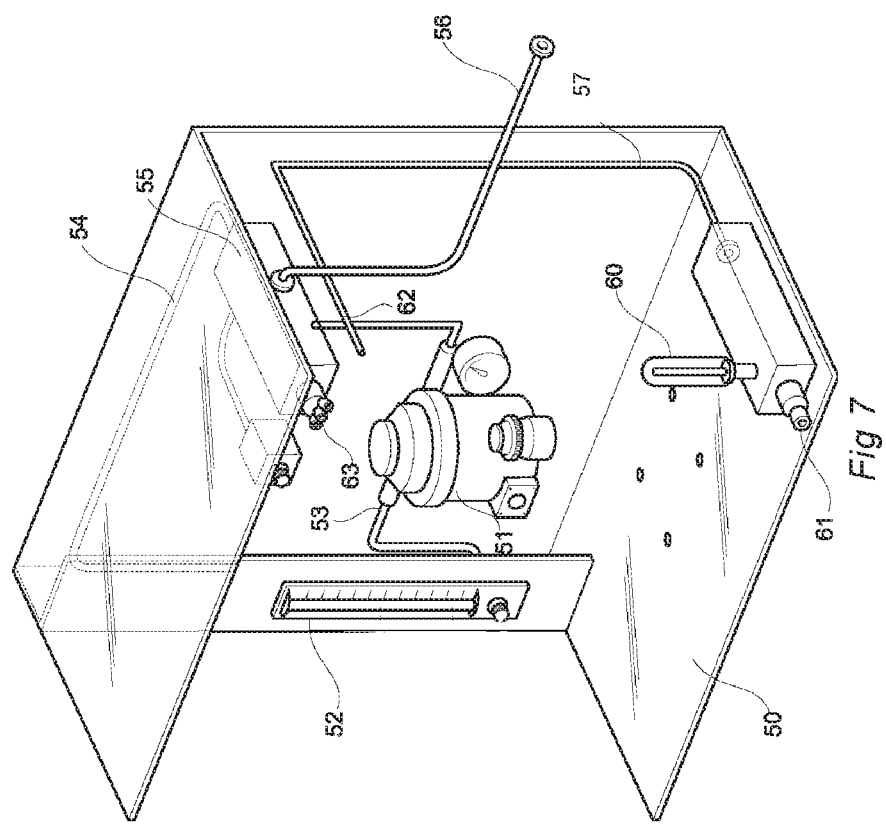

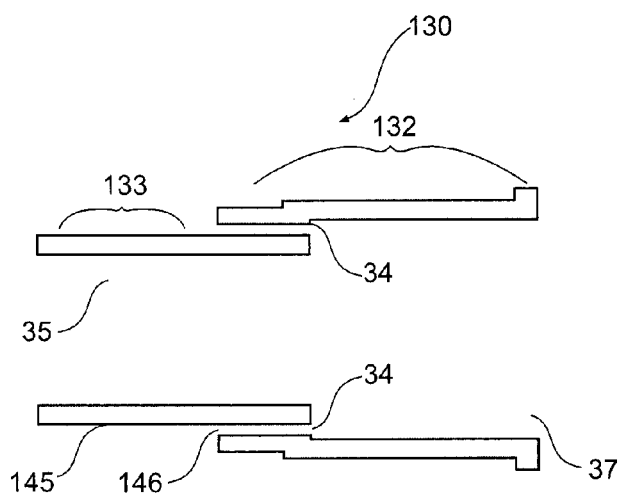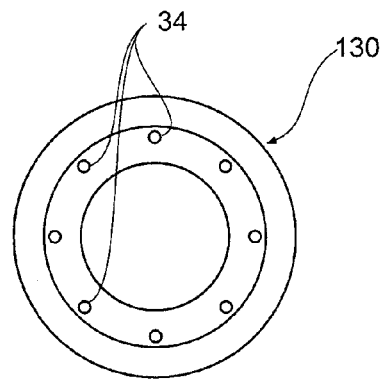
Fig 9a    Fig 9b
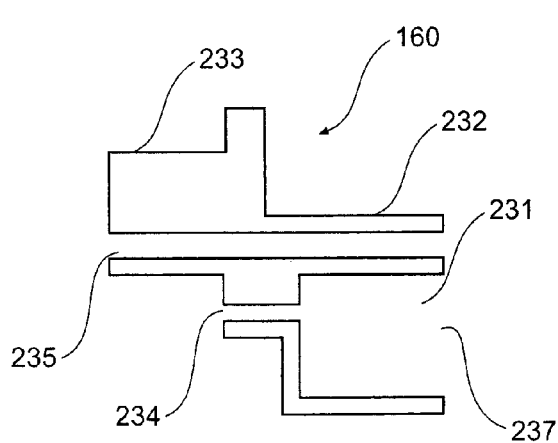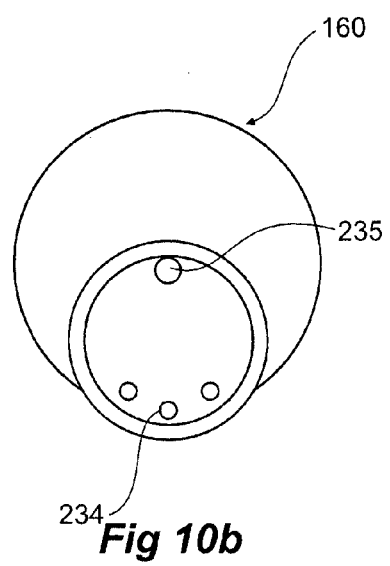
Fig 10a    Fig 10b

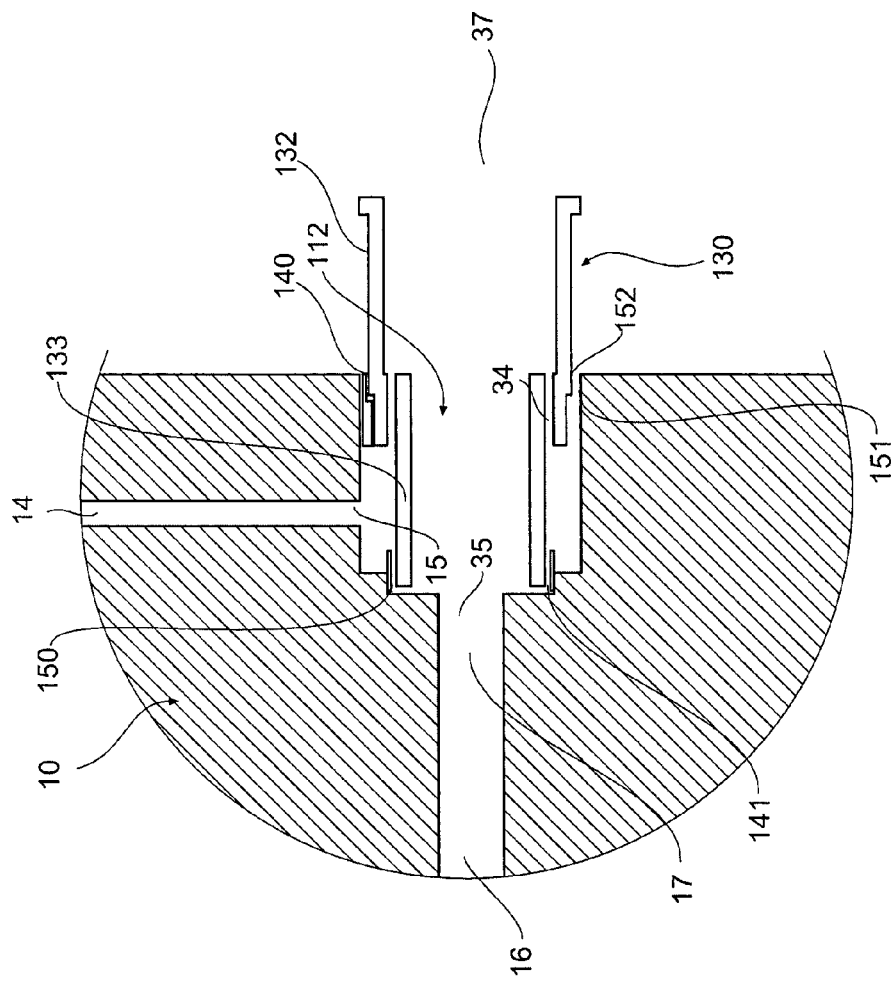
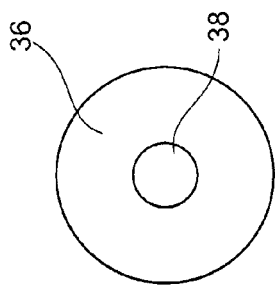
*Fig 17*
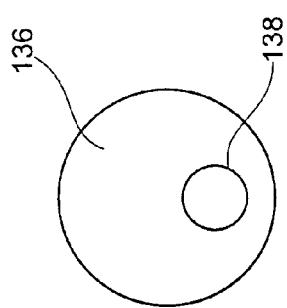
*Fig 18*

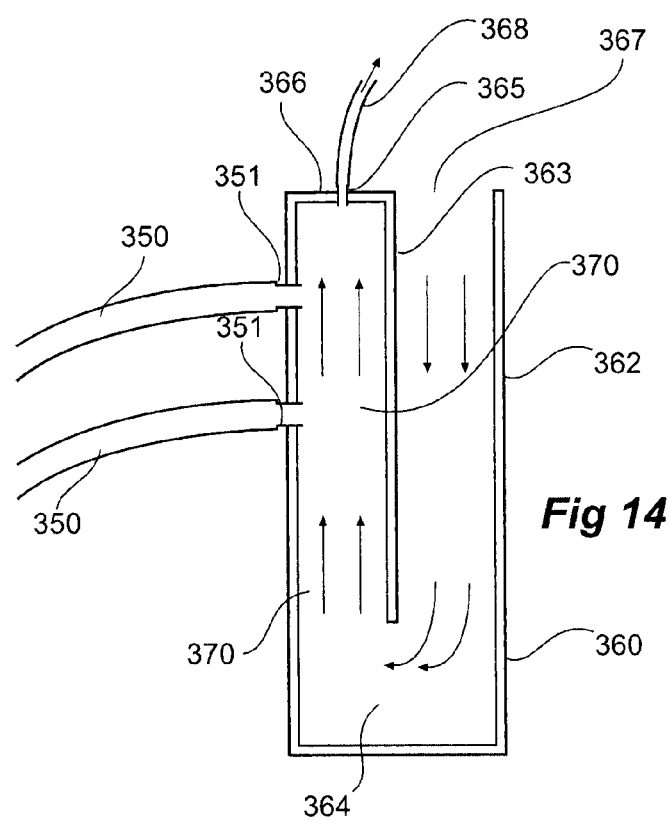
*Fig 14*
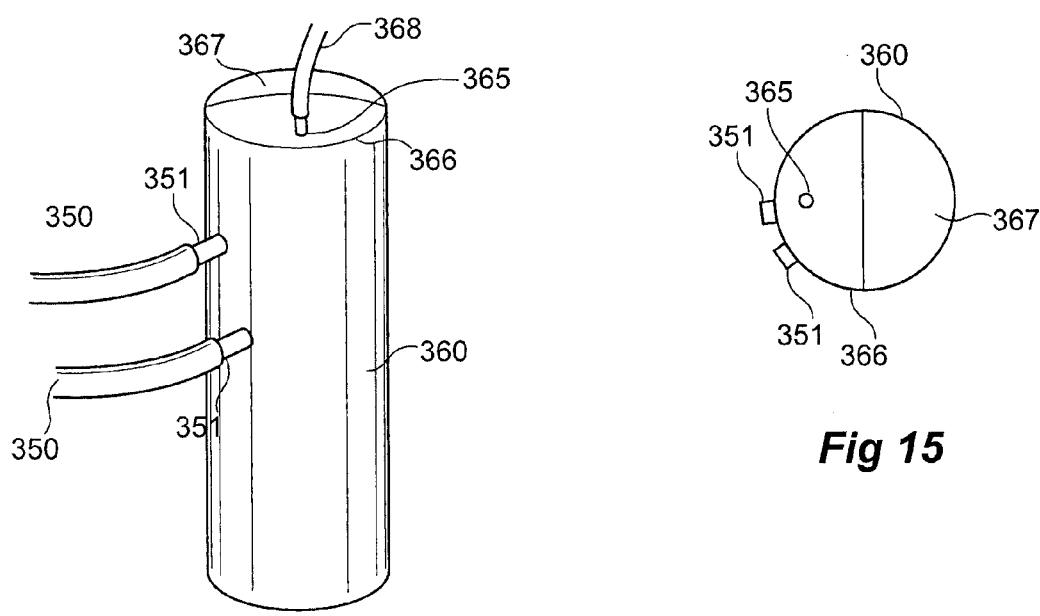
*Fig 16*
*Fig 15*

METHOD AND APPARATUS FOR DELIVERING A FLUID TO A PATIENT

CROSS REFERENCE TO RELATED APPLICATIONS

The present application is a National Phase Application of International Application No. PCT/AU2010/000975, filed Aug. 3, 2010, which claims priority to Australian Patent Applications No. 2009903614, filed Aug. 3, 2009, which applications are incorporated herein fully by this reference.

FIELD OF THE INVENTION

The present invention relates to an improved apparatus and method for delivering a fluid to a human or animal subject, and particularly, but not exclusively, to an improved apparatus and method for delivering a fluid to a small animal subject.

BACKGROUND OF THE INVENTION

In anaesthesia, anaesthetic gases are delivered to subjects, such as patients, usually utilizing one of a number of types of anaesthetic circuit. The anaesthetic circuit is arranged to deliver a regulated dose of anaesthetic to the subject along with oxygen or a gas mixture including oxygen or atmospheric air. It is important that the subject be supplied with and breathes a correct mixture of oxygen and anaesthetic gas. Too little oxygen reaching the lungs, or too much re-breathed $CO_2$ reaching the lungs, can lead to significant problems, including hypoxia and death.

An important issue with anaesthetic circuits is the issue of "dead space". This is the volume of gas at expiration that the subject must re-breathe before getting gas that does not contain carbon dioxide. The dead space includes the subject's own air passageway dead space (e.g. trachea, or cavity) and, with anaesthetic circuits, a certain amount of "machine dead space".

The more machine dead space the more volume a subject must breathe in before they breathe gas that does not contain carbon dioxide. For adult humans and large animals, the amount of machine dead space is often not large compared to the anatomic dead space and the total volume of their airways. For small animals and small humans, however, the amount of machine dead space can become critical. For example, a two kilogram animal may have a total tidal volume of 20-30 mls. A third of this volume will be anatomic dead space. Any additional machine dead space may cause significant issues for anaesthesia. For example, an extra 10 mls of dead space can cause the animal to hyperventilate, become hypoxic and die.

Even if patients do not become hypoxic, the delivery of anaesthetic is much less efficient and it is more difficult to achieve anaesthesia.

To address the machine dead space issue, it is common to intubate patients (introducing a tube into the trachea). For small animals and infants, however, this is not always a satisfactory solution. With smaller airways, the diameter of the tube lumen becomes so small that the patient may not be able to draw enough gas into their lungs (the small diameter tubing provides significant resistance to inspiration).

Small, tight fitting masks have been designed for small animals and infants. Nevertheless, even small masks still add dead space which can be significant.

In fact, dead space issues for small animals such as lab animals (e.g. rats, mice and other lab animals) are so significant that apparatus and methods other than traditional delivery of anaesthetic gas mixture via masks or tubes must be contemplated. With slow acting anaesthetics, such as ether, simple systems that merely provide the anaesthetic vapour or liquid direct to the patient, e.g. ether from cotton wool balls onto the nose of the patient may be used. Such traditional anaesthetics, however, are environmentally unsound and have generally fallen out of use.

Perhaps the most commonly used systems in the prior art for small lab animals are open systems which actively pump anaesthetic and waste gas over the respiratory openings of the subject. The patient is placed with their respiratory orifice next to a large opening of a delivery system. The anaesthetic is essentially pumped to the subject's respiratory orifice. Waste gas is sucked out of the system by pumping. That is, the waste gas is actively removed by pumping. These systems are high flow systems. Modern anaesthetics such as methyoxyflurane can be used in these systems, but large amounts of anaesthetic, in the order of a liter per minute in some cases, are used. This is very expensive. Also, a significant amount of anaesthetic may leak into the surrounding environment from the open system, causing a potential health hazard. The active provision and removal of anaesthetic/gas mixture is therefore very wasteful and expensive.

With these systems, it is also very difficult to ensure that a subject is anesthetized with any precision. It is difficult to tell with any accuracy the concentrations of anaesthetic gas mixture at the patient's respiratory orifice. There will be, for example, entrainment of room air because of the open system, which will dilute the anaesthetic gas mixture. It can therefore be very difficult to anesthetize subjects with this system and maintain anaesthetic depth.

It is often required that a number of subjects be anesthetized at the same time. It is common, for example, where a number of lab animals are being treated at the same time. They may be being anesthetized, for example, in order to have blood samples taken so that lab experiments can be monitored, or they may be being anesthetized for other reasons. It is known to anesthetize a plurality of animals in an induction chamber. Again, however, a lot of anaesthetic is used to fill the induction chamber sufficiently to anesthetize the animals, and little or no precision in the amount of anaesthetic administered is possible. This can lead to accidents, not maintaining anaesthesia, or even death of the subjects.

It is known to use active systems such as discussed above, to anesthetize a plurality of animals at the same time. This essentially means reproducing the open system for each subject to be anesthetized. A separate open mask is provided for each subject and a separate line from the anaesthetic machine for each subject is required. This is complex, difficult to set up, and difficult to ensure that the animals are placed appropriately by each respective mask and maintained there while anaesthetic takes effect. The number of lines and flow meters required for the anaesthetic machine is also complex and expensive.

The present Applicant's earlier patent application, International Patent Application No. PCT/AU2007/001920, discloses a method and apparatus for delivering anaesthetic to a patient which delivers the anaesthetic by inducing an anaesthetic flow to reduce re-breathing of fluid exhausted from the respiratory tract of the subject. The exhaled fluid is exhausted from a position distal to the proximal position to the respiratory tract of introduction fresh fluid to the subject. The contents of this application are incorporated herein by reference.

SUMMARY OF THE INVENTION

In accordance with a first aspect, the present invention provides an apparatus for facilitating delivery of a fluid to the respiratory tract of a subject, comprising a fluid line substrate having conduits formed therein for transmission of fluid, a support for stabilizing the substrate with respect to a supporting surface, and a subject port formed in the substrate and arranged for delivery of fluid to a subject placed proximate the subject port, the conduits comprising a first conduit having a first conduit outlet which opens into the subject port, whereby fluid may be delivered to the subject port via the first conduit, and a second conduit having a second conduit inlet communicating with the subject port, whereby fluid may flow from the subject port into the second conduit, the second conduit inlet being positioned distally with respect to the subject port from the first conduit outlet whereby to induce a fluid flow to reduce re-breathing by the subject of fluid exhausted from the respiratory tract.

In an embodiment, in use the fresh fluid is introduced proximate the respiratory opening of the subject and the fluid flow is such that the introduced fluid flows over the respiratory opening of the subject and then towards the second conduit inlet. It is an advantage of at least an embodiment that, where the fluid is an anaesthetic gas mix, then a relatively low flow system can be used because there is no significant amount of dead space and the subject can respire normally.

In an embodiment, the apparatus further comprises a first conduit inlet formed in the fluid line substrate and arranged to receive input fluid and a second conduit outlet formed in the fluid line substrate for exhausting output fluid.

In an embodiment, the substrate is a block of material and the support is a first surface which arranged to support the block on a supporting surface. In an embodiment, the subject port is formed in a further surface of the block, the further surface being adjacent the first surface. In an embodiment, the block is in the form of a rectangular prism and the first surface is one or more of the surfaces of the rectangular prism which contiguous with the first surface. In an embodiment, a first conduit inlet and second conduit outlet are formed in a surface opposite the further surface. In an embodiment, the material may be a metal.

In the embodiment where the substrate is a block of material, such as metal, this has the advantage that the block is stable, being stably supported by a supporting surface, and therefore can assist in stabilizing the fluid lines and the subject. Where the subject is a small animal or Very Small Animal (VSA) this has the advantage that the fluid lines are stably supported and do not require tricky manipulation.

In an embodiment, the apparatus further comprises a mating arrangement for mating the subject port with a mask apparatus. The mask apparatus comprises an enclosure having a first opening arranged to fit over a respiratory opening of a subject, and at least one second opening arranged to receive fluid provided to the subject port from the first conduit outlet. In an embodiment, the mask apparatus also has a third opening arranged to communicate with the second conduit inlet. In an embodiment, the mating arrangement comprises a socket portion of a subject port arranged to receive a plug portion of the enclosure.

In the embodiment where a mating arrangement is provided for mating with a mask apparatus, there is the advantage that a separate mask apparatus can be provided for facilitating delivery of fluid to the subject. Dimensions of the mask apparatus may therefore be adjusted to suit particular subjects without having to change dimensions of the fluid line substrate, for example. Further, the mask apparatus can be removed from the fluid line substrate and disposed of or cleaned separately.

In an embodiment, the apparatus further comprises an adjustment mechanism arranged to enable adjustment of fluid flow to the first conduit outlet. The adjustment mechanism may comprise an adjustable plug arranged to project within the first conduit by a variable amount.

In an embodiment, the apparatus comprises a plurality of fluid line substrates comprising a respective plurality of first conduits, second conduits and subject ports for facilitating delivery of fluid to a respective plurality of subjects placed proximate the respective subject ports. In an embodiment, the plurality of fluid line substrates are integrated as a single combined fluid line substrate.

In the embodiment where there are a plurality of fluid line substrates, this has the advantage that a plurality of subjects can be treated at the same time. For example, where the subjects are small animals or VSAs, a number of them can be anesthetized at the same time using a single apparatus. This greatly reduces complexity compared with the prior art where, for example, with lab animals, it is necessary to deal with a plurality of separate fluid line systems (difficult to manipulate) to anesthetize a plurality of subjects. In an embodiment, a plurality of first conduits is connected by a first common conduit to form a manifold. The first conduit inlet connects to the first common conduit and to the plurality of first conduits. In an embodiment, the plurality of second conduits open into a second common conduit to form a manifold that opens into the second conduit outlet. This arrangement has the advantage that a single inlet line from an anaesthetic machine and a single outlet line may serve to deal with a plurality of fluid lines for a plurality of subjects. This, again, reduces complexity as compared with the prior art.

In an embodiment, the apparatus further comprises a heating arrangement for heating the fluid line substrate. The heating arrangement may comprise at least one heating conduit formed in the substrate and arranged to receive a heated fluid. In another embodiment, the heating arrangement may comprise a conduit arranged to receive a heating element, such as an electrical heating element, or the heating element may be embedded in the substrate.

In an embodiment the apparatus is dimensioned to suit small animals or VSAs. In an embodiment, the apparatus is dimensioned to suit subjects of 500 grams or less. It may be suitable for rats and mice as subjects. In an embodiment, the fluid is an anaesthetic gas mix.

In accordance with a second aspect the present invention provides an apparatus for facilitating delivery of a fluid to the respiratory tract of a subject, comprising a fluid line substrate having conduits formed therein for transmission of fluid, a support for stabilizing the substrate with respect to a supporting surface, and a subject port formed in the substrate and arranged for delivery of fluid to a subject placed proximate the subject port, the conduits comprising a first conduit having a first conduit outlet which opens into the subject port, whereby fluid may be delivered to the subject port via the first conduit, and a mating arrangement for mating the subject port with a mask apparatus, the mask apparatus comprising an enclosure having a first opening arranged to fit over a respiratory opening of the subject and at least one second opening arranged to receive fluid provided to the subject port from the first conduit outlet.

This aspect of the invention may include any or all of the features of the embodiments of the first aspect of the invention discussed above.

In accordance with a third aspect the present invention provides an apparatus for facilitating delivery of a fluid to the respiratory tracts of a plurality of subjects, comprising a fluid line substrate comprising a plurality of subject fluid line conduits formed therein for transmission of fluid, and a plurality of subject ports formed in the substrate, each subject port being arranged to deliver fluid to a subject placed proximate the subject port, each subject fluid line conduit comprising a first conduit having a first conduit outlet which opens into a respective subject port, whereby fluid may be delivered to the subject port via the first conduit.

This aspect of the invention may include any or all of the features of the embodiments of the first aspect of the invention discussed above.

In accordance with a fourth aspect, the present invention provides a mask apparatus for facilitating delivery of fluid to the respiratory tract of a subject, the mask apparatus comprising an enclosure having a first portion arranged to fit over a respiratory opening of the subject to deliver fluid to the respiratory opening of the subject, a mating arrangement arranged to mate with a fluid line apparatus comprising a fluid line substrate comprising a first conduit formed therein for transmission of fluid, and a subject port formed in the substrate, the first conduit having a first conduit outlet which opens into the subject port, the mask apparatus further comprising an inlet arranged to communicate with the first conduit outlet when the mask apparatus is mated with the fluid line substrate, whereby fluid may be delivered to the subject via the first conduit outlet and the first portion of the mask.

In an embodiment, the mask apparatus further comprises an outlet from the enclosure, the outlet being positioned distally with respect to the inlet, whereby to induce a fluid flow to reduce re-breathing of fluid exhausted from the respiratory tract of the subject.

In an embodiment, the enclosure if of a size appropriate to suit a small animal or a VSA (being an animal of 500 grams or less) as the subject.

In an embodiment, the mating arrangement comprises a plug portion of the enclosure which is arranged to mate with the subject port of the fluid line substrate.

In an embodiment, the mask enclosure has a substantially cylindrical transverse cross section. The cylindrical cross section may be any cross sectional shape e.g. circular, ovoid, rectangular, irregular. In an embodiment the inlet is arranged such that fluid is introduced into the enclosure at least at opposite sides of the cylinder. In an embodiment, the inlet comprises a plurality of orifices in the enclosure positioned about the periphery of the cylindrical cross section.

In an embodiment, the mask apparatus further comprises a diaphragm arranged to fit over an opening in the first portion, the diaphragm having a diaphragm opening to receive the respiratory opening of the subject. In an embodiment, the diaphragm is arranged to receive the nose and mouth of a subject through the diaphragm opening and the periphery of the opening abuts the nose and mouth anatomy of the subject. This may have the advantage that the subject's mouth and nose anatomy is retained by the diaphragm. Further, the fluid delivery system is at least partially sealed by the diaphragm to facilitate low flow of fluid (e.g. low flow of anaesthetic where the fluid is anaesthetic).

In an embodiment, the fluid line apparatus may be the apparatus of any one of the first to third aspects of the invention.

In accordance with a fifth aspect, the present invention provides a system for delivering fluid to the respiratory tract of a subject, comprising an apparatus in accordance with any one of the first to third aspects of the invention and a mask apparatus according to the fourth aspect of the invention.

In accordance with a sixth aspect, the present invention provides an anaesthetic machine for use with an apparatus in accordance with the third aspect of the invention, the machine comprising an anaesthetic vaporizer for providing anaesthetic as the fluid, a single flow meter and a single line for providing an anaesthetic gas mixture to the fluid line substrate, whereby to provide anaesthetic to the respiratory tracts of the plurality of subjects.

In an embodiment, the anaesthetic machine is arranged to provide relatively low flow of anaesthetic.

In accordance with a seventh aspect, the present invention provides an anaesthetic delivery system for delivering anaesthetic to subjects, comprising an anaesthetic machine and an apparatus in accordance with any one of the first to third aspects of the invention.

In an embodiment, the anaesthetic delivery system further comprises a mask apparatus in accordance with the fourth aspect of the invention.

In accordance with an eighth aspect, the present invention provides a method of operating an anaesthetic machine in accordance with the sixth aspect of the invention, comprising the steps of operating the machine to provide relatively low flow of anaesthetic.

In accordance with a ninth aspect, the present invention provides a method of operating an anaesthetic delivery system in accordance with the seventh aspect of the invention, comprising the step of operating the system to provide relatively low flow of anaesthetic gas mixture.

BRIEF DESCRIPTION OF THE DRAWINGS

Features and advantages of the present invention will become apparent from the following description of embodiments thereof, by way of example only, with reference to the accompanying drawings, in which:

FIG. 1 is a diagram of a prior art "open mask" system for delivering anaesthetic to a subject;

FIG. 2 is a machine end diagram of the prior art system of FIG. 1;

FIG. 3 is a schematic perspective diagram of an embodiment of the present invention, showing internal configuration, being a view from one side of the apparatus;

FIG. 4 is a view from an opposite side of the apparatus of FIG. 3;

FIG. 5 is a longitudinal cross sectional view of a mask apparatus in accordance with an embodiment of the present invention;

FIG. 6 is a front view of the mask apparatus of FIG. 5;

FIG. 7 is a perspective view of an anaesthetic machine in accordance with an embodiment of the present invention;

FIG. 8 is a perspective view diagram of an apparatus in accordance with a further embodiment of the present invention, showing internal configuration;

FIG. 9A is a cross-sectional view of a mask apparatus in accordance with an embodiment of the present invention;

FIG. 9B is a front view of the mask apparatus of FIG. 9A;

FIG. 10A is a longitudinal cross-sectional view of a further mask apparatus in accordance with an embodiment of the present invention;

FIG. 10B is a view from the front of the mask apparatus of FIG. 10A;

FIG. 11 is a side cross-sectional view of the mask apparatus of FIG. 9A showing it mated with a portion of a fluid line substrate in accordance with an embodiment of the present invention;

FIG. 14 is a longitudinal cross-sectional view of an apparatus for evacuating waste gases in accordance with an embodiment of the present invention;

FIG. 15 is a view from the top of the apparatus of FIG. 14;

FIG. 16 is a perspective view from above and one side of the apparatus of FIG. 14;

FIG. 17 is a front view of a diaphragm for use with a mask apparatus in accordance with an embodiment of the present invention; and FIG. 18 is a front view of a further diaphragm for use with a mask apparatus in accordance with an embodiment of the present invention.

DETAILED DESCRIPTION OF EMBODIMENTS

As discussed in the preamble of this specification, delivery of anaesthetic to small animals and VSAs is difficult, particularly with modern anaesthetics like methyoxyflurane. Small animals and VSAs in particular have small respiratory volumes, and therefore the amount of dead space that is in any anaesthetic delivery system is critical. Typical volume of a mouse breath, for example, is less than 1 mm$^3$. In order to combat dead space issues, it is known to use "high flow" systems to anesthetize subjects.

Figure 1:
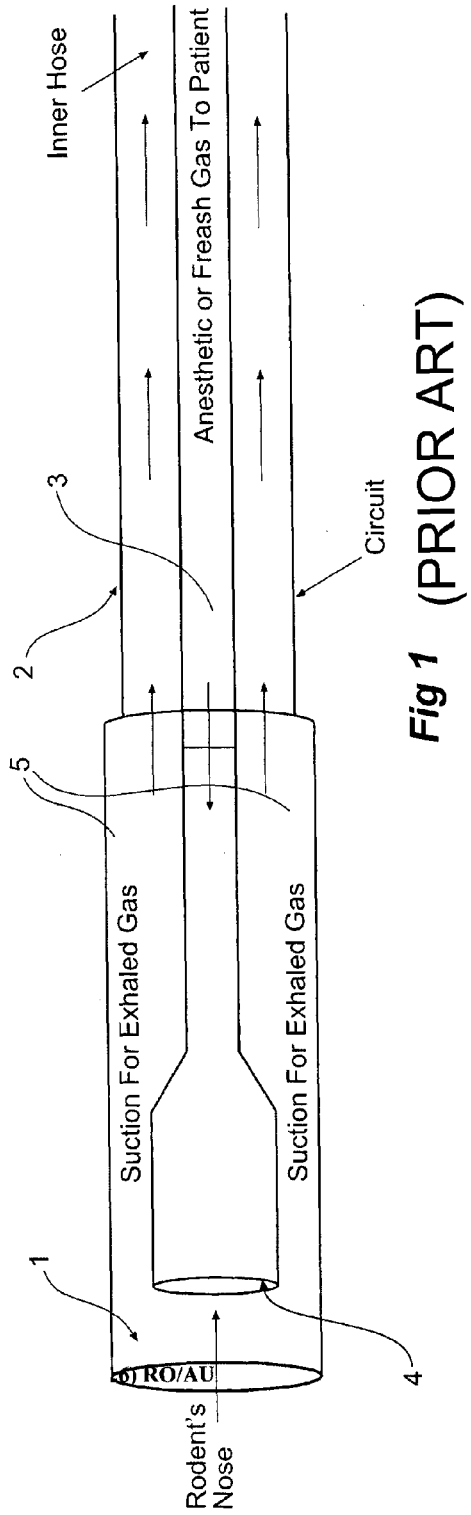
Figure 2:
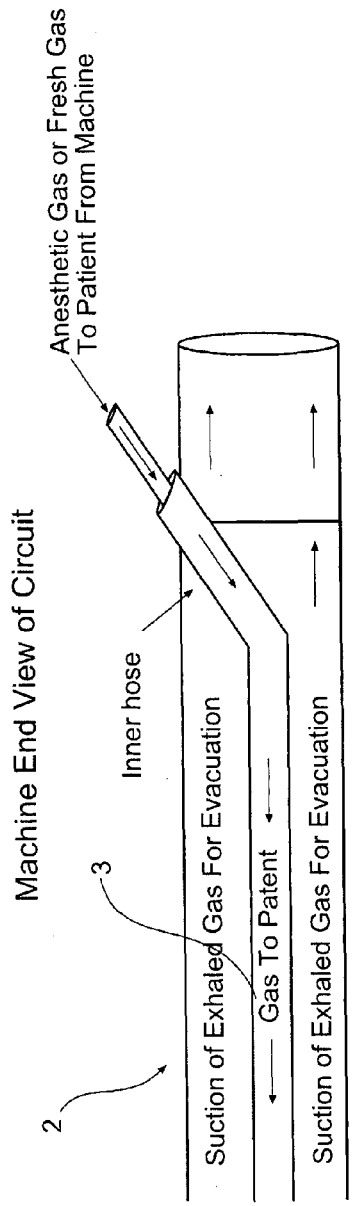

Referring to FIGS. 1 and 2, a diagram of a typical high flow system is shown.

The system comprises a "mask" 1 attached to the end of an anaesthetic circuit (generally designated by reference numeral 2). The mask 1 is not really a mask in the sense that it seals to the face of the subject. Rather, the subject is placed next to the mask or with the respiratory orifice projecting into the mask (e.g. nose and mouth of a rodent). Anaesthetic is then pumped along a central line 3 to the mask 1 via central line opening 4. The fresh gas is pushed to the subject at a relatively high pressure and exhaled gas sucked out using a suction pump along a line 5 coaxial with the central anaesthetic supply line 3.

High flow systems such as this have the disadvantage that they use a very large amount of anaesthetic. For example, in systems for anesthetizing rodents such as mice, an open high flow system such as shown in FIG. 1 and FIG. 2 may use upwards of a liter per minute of anaesthetic and pump in order of six liters per minute of anaesthetic/gas mixture. This is far more than would be necessary to anesthetize a small subject in a closed system. It is necessary to provide these high flows in order to ensure anaesthesia in an open system. Further, because of entrainment of air from the external environment, the amount of anaesthetic actually delivered to the respiratory orifice of the subject cannot be known with any precision. Anaesthetic depth is therefore unreliable and, in some cases, subjects may wake up during the process.

Such systems are therefore expensive (using lots of expensive anaesthetic), unreliable and environmentally polluting (as anaesthetic may escape into the surrounding environment).

Referring to FIGS. 3 and 4, an embodiment of an apparatus in accordance with the present invention will now be described.

The apparatus comprises a fluid line substrate 10 which has conduits formed therein for transmission of fluid and a support 11 for supporting the fluid line substrate 10 with respect to a supporting surface (not shown, but may be a table, lab bench or other supporting surface). In this example embodiment, the support 11 is one side of what is a rectangular prism form block substrate 10.

A subject port 12 is formed in one surface 13 of the substrate 10. The subject port 12 in this example is a cylindrical bore in the substrate 10. The bore is circular in cross section in this example but need not be and could be any cross section e.g. ovoid, square, irregular. In this embodiment the block is of metal with the conduits bored into it. The substrate 10 may be of any other material, however, and may be of plastics (for example, a hard polypropylene plastic which is machineable, such as Devron™, or other similar plastic), for example.

In use, a subject, such as a VSA is placed with their respiratory orifice proximate the subject port 12 so that fluid can be delivered to the respiratory orifice of the subject. In this embodiment (see later) a mask apparatus is mated with the subject port 12 and the fluid is delivered to the subject via the mask apparatus. In other embodiments, however, a mask apparatus may not be necessary, and the fluid may be delivered from the subject port 12 directly to the subject.

The conduits include a first conduit 14 having a first conduit outlet 15 which opens into the subject port 12. Fluid may be delivered to the subject port 12 via the first conduit outlet 15.

A second conduit 16 has a second conduit inlet 17 which communicates with the subject port 12. In operation, fluid may flow into the subject port 12 from the first conduit outlet 15 and from the subject port 12 into the second conduit 16 via the second conduit inlet 17.

The second conduit inlet 17 is positioned distally with respect to the first conduit outlet 15, with regard to the subject port 12. In use, this induces a fluid flow which reduces re-breathing by the subject of fluid exhausted from their respiratory tract. It minimises dead space by passing the introduced fluid from the first conduit outlet 15 over the subject's respiratory orifice (proximate the subject port 12) and removing the exhausted fluid from the distally arranged second conduit inlet 17.

In this embodiment, the subject port 12, the first conduit 14 and the second conduit 16 are all cylindrical bores bored from the substrate 10. Note that the cylinders may be of any cross sectional shape, but are circular in this embodiment.

A first conduit inlet 18 is provided in a surface 19 opposite the surface 13 mounting the subject port 12. Also in this embodiment, a second conduit outlet 20 is provided in the surface 19. In use, the first conduit inlet 18 is connected to a fluid line for providing fluid, such as a fluid line from an anaesthetic machine. The second conduit outlet 20 may be connected to a scrubbing system for scrubbing waste gas from anaesthetic and returning the waste gas into the anaesthetic circuit (closed system) or merely exhausting the waste gas (open system).

In this embodiment, as discussed above, the conduits are bored from the substrate 10. The first conduit is formed by boring in from the surface 19 to form the first conduit inlet 18 and a first leg 14A of the first conduit 14, the first leg 14A extending towards the face 13 mounting the subject port 12. A second leg 14B is formed by boring in from a top surface 21 of the substrate 10. The second leg 14B crosses the first leg 14A so as to form a continuous first conduit 14. A sealing member 22, in this embodiment in the form of a screw, then seals one end of the leg 14B. In this embodiment, the seating member 22 acts as an adjustment mechanism and is adjustable, by screwing it further into or further out of the leg 14B across the face of the leg 14A where it connects to the leg 14B. Adjustment of the member 22 can be used to regulate the amount of flow of gas within the first conduit 14, to adjust flow to the subject port 12.

A mask apparatus in accordance with an embodiment of the present invention is illustrated in FIGS. 5 and 6. In this embodiment, the mask apparatus 30 comprises an enclosure 31 having a first portion 32 which is arranged to fit over a respiratory opening of the subject to deliver fluid to the respiratory opening of the subject. It also comprises a mating arrangement, in this embodiment being in the form of a second portion 33 of the enclosure 31 which is arranged to mate with a fluid line apparatus such as the fluid line apparatus 10 of FIG. 3 and FIG. 4 (and fluid line apparatus of FIG. 8, to be described later).

The mask apparatus 30 comprises an inlet 34 which is arranged to communicate with the first conduit outlet of the fluid line apparatus (e.g. outlet 15 of FIG. 3), when the mask apparatus 30 is mated with the fluid line apparatus, so that fluid may be delivered to the subject via the first conduit outlet and the first portion 32 of the mask apparatus.

The mask apparatus also comprises an outlet 35 which is positioned distally with respect to the inlet 34 to induce a fluid flow to reduce re-breathing of fluid exhausted from the respiratory tract of the subject.

In this embodiment, the inlet 34 in fact comprises a plurality of holes (see FIG. 6) spaced about the periphery of the cylindrical cross-section of the mask apparatus 30. When the respiratory orifice of the subject is placed within the portion 32, then the inlets 34 pass gas over the orifice of the subject and waste gas is removed distally from port 35. This reduces re-breathing and minimises dead space.

The cylindrical cross-section of the mask apparatus 30 is circular in this embodiment, but may be any shape (e.g. ovoid, square, irregular).

A flexible diaphragm 36 is mounted over an opening 37 to the first portion 32 of the mask apparatus 30. The diaphragm 36 has a central opening 38. In operation, the subject's mouth and nose anatomy is placed through the central opening 38. The diaphragm 36 provides at least a partial seal about the mouth and nose anatomy of the subject, in this embodiment. The diaphragm 36 may be of flexible material, such as rubber. This facilitates the ability to have a low flow system for providing and removing fluid. It reduces entrainment of external air into the system. It also may facilitate holding the subject so that their respiratory orifice is maintained in portion 32 of the mask apparatus 30. In operation, the subjects nose and mouth anatomy may be pushed into the central opening 38 of the diaphragm, the subject anesthetised (when the fluid is anaesthetic) and then the subjects nose and mouth anatomy may be held by the diaphragm 36. Another of the problems of prior art open mask systems is that the subject's nose and mouth anatomy can fall away from the opening of the mask. In this embodiment, the diaphragm may prevent this.

In this embodiment, the mask apparatus 30 is of clear or white plastics. This can facilitate the use of further sensors to monitor the subject (see later).

The mating arrangement for mating with the fluid line apparatus comprises a plug portion 33 of the mask apparatus 30. Referring to FIGS. 3 and 4, the plug portion 33 of the mask apparatus 30 fits into a "socket" formed by the subject port 12. The plug portion 33 of the mask apparatus 30 is dimensioned for a snug-fit within the subject port 12. A pair of circumferential gaskets 40 and 41, spaced from each other within the subject port provide a seal with the plug portion 33 of the mask apparatus 30. The first conduit outlet 15 opens into the gap between the gaskets 40 and 41, as can be seen from FIGS. 3 and 4.

The plug portion 33 of the mask apparatus 30 is formed with a circumferential slot 45 therein. In use, this slot 45 communicates with the first conduit outlet 15. An outer wall 46 of the slot 45 mounts the mask inlets 34. Fluid is transmitted from the first conduit outlet 15 in use via the slot 45 to mask inlets 34 to the subject portion 32 of the mask apparatus 30.

Because the mask apparatus 30 is removable from the fluid line apparatus it can be cleaned separately or even disposed of.

The fluid line apparatus acts to stabilise the fluid lines and also stabilise the subject with respect to the fluid lines.

In this embodiment, the mask apparatus 30 and fluid line apparatus 10 (and also the fluid line apparatus of FIG. 8, to be described later) are dimensioned for use with small animals and Very Small Animals (VSAs). In an embodiment, the mask 32 may have a first opening 37 which is of a dimension of 50 millimeters or less, or 25 millimeters or less. It may be 50 millimeters or less in length or 20 millimeters or less. In this embodiment, the width and length dimensions are 23 millimeters and 18 millimeters respectively. The outlet of the mask may have a dimension of 50 millimeters or less or 20 millimeters or less. In this embodiment it is 15 millimeters. Please note that these dimensions are examples only and the invention is not limited to these dimensions. Depending on the size of the subject that the arrangement is designed for, the dimensions may vary.

The dimensions of the fluid line apparatus will vary accordingly to match the mask apparatus dimensions.

The fluid line apparatus and mask embodiment described above may be suitable for anesthetizing VSAs, such as rodents, such as mice for example.

FIG. 9A and FIG. 9B illustrate a further embodiment of a mask apparatus, in accordance with the present invention. In this embodiment, the same reference numerals as used in FIGS. 5 and 6 have been used to denote similar components. No further description will be given of these components. This embodiment of the mask apparatus has been designated by reference numeral 130.

In this embodiment, a plug portion 133 of the mask apparatus 130 is not formed with a slot. Instead, the plug portion 133 is a tower diameter 145 portion than the first portion 132. A step 146 is formed connecting the first portion 132 and the plug portion 133. In operation, the shape of the subject port 12 in the substrate 10 is arranged to receive this non slotted plug portion 133. It has been found that this type of mask apparatus 130 is easier to injection mould from plastics.

FIG. 11 shows a portion of a substrate 10 having a modified subject port 112, modified over that of the embodiment of FIGS. 3 and 4. Subject port 112 is shown mated with a mask apparatus 130 of FIGS. 9A and 9B. In this embodiment, a pair of circumferential gaskets 140 and 141 facilitate a seal with the mask apparatus 130. Gasket 141 lines a lower diameter step 150 at the distal end of the subject port 112.

The step 150 is arranged to receive the distal end of the mask apparatus plug 133 in a snug fit.

The proximal end 112 of the subject port has a larger diameter circumferential wall 151 which provides a snug fit with the distal end of the first part 132 of the mask apparatus 130. A shoulder 152 is formed circumferentially about the first part 132 of the mask apparatus 130, and in use this buts up against the circumferential edge of the port 112. The first conduit outlet 15 of the substrate 112 communicates with the inlet 34 of the mask apparatus 130, in use. The outlet 35 of the mask 130 communicates in use with the second conduit inlet 17 of the substrate 10.

The mask apparatus 130, 30 and fluid line substrate 10 of these embodiments are designed for VSAs such as rodents. VSAs can vary greatly in size, however. For example, a rat is far larger than a mouse.

If the embodiment of FIGS. 3, 4, 5, 6, 9A, 9B and 11 were sized for a rat, for example, then it may be difficult to use with a smaller animal such as a mouse (although it may be possible). For example, it may be difficult to place the nose of the mouse into the opening 37 of the mask apparatus 30, 130, when the mask apparatus is placed in the subject port 112, 12. This is because the mask apparatus 130, 30 may be too far off the support surface (eg table).

Figure 12:
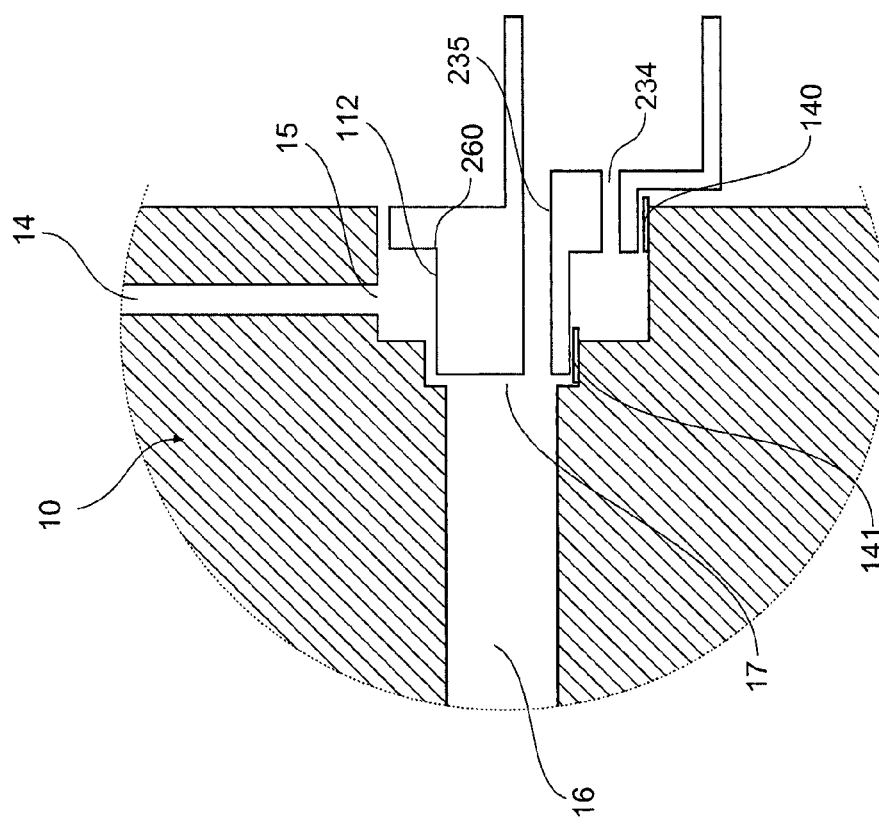
FIG. 12 is a cross-sectional view of the mask apparatus of FIG. 10A showing it mated with a portion of a fluid line substrate in accordance with an embodiment of the present invention.

FIGS. 10A, 10B and 12 show a further embodiment of a mask apparatus 160, which may address this problem.

The mask apparatus 160, comprises a first portion 232 comprising walls defining an enclosure 231 which is arranged to receive a respiratory opening of the subject (eg a small animal such as a mouse).

In this embodiment a mating arrangement comprises a second portion 233 in the form of a plug body arranged to fit into a subject port 112 of a fluid line substrate 10 (FIG. 12).

In the above-described embodiments of the mask apparatus 30, 131, the first 33, 133 and second 32, 132 portions are concentric. In the embodiment of FIGS. 10A and 10B, the first 232 and second 233 portions are eccentric. 232 is offset relative to second plug portion 233 so that, in use, the opening 237 defined by the enclosure 231 is offset and in use may sit lower than the subject port 112. It may therefore allow the head of a smaller animal to fit into the opening 237 without difficulty.

The mask apparatus 160 comprises an inlet 234 which, in use is arranged to communicate with the first conduit outlet 15. The inlets 234 are formed at the bottom part of the mask apparatus 160 and there are a plurality of them, as best illustrated in FIG. 10B.

The mask apparatus 160 also comprises a outlet 235 which, in use, is arranged to communicate with a second conduit inlet 17 of the fluid line substrate 10.

Referring to FIG. 12, it can be seen that the plug portion 233 distal end mates snugly with the gasket 141 in the fluid inlet substrate 10. A step 250 is formed at the proximal portion of the plug body 233. The outer part of the step 260 mates snugly with gasket 140 of the fluid line substrate 10.

It will be appreciated that variations of the mask apparatus may be made, with various offsets, between the plug body and the opening for receiving an animal, to cater for various sizes of animals.

FIG. 17 is a front view of the gasket 36 that might be used over the opening 37 of a mask apparatus such as those of the embodiments of FIGS. 5, 6, 9A, 9B, 10A, 10B. The opening 38 in the gasket is arranged to securely receive the mouth and nose anatomy of the animal. In this embodiment, the opening 38 is placed centrally in the gasket 36.

FIG. 18 shows an alternative embodiment 136 of a gasket for the mask apparatus. In this embodiment, the opening 138 in the gasket is placed off-centre. This may also facilitate operation with a variety of different sized animals.

It will be appreciated that openings 138 may be offset at any place in the gasket 136 area.

An anaesthetic machine which may be used in a system with the mask arrangement of FIGS. 5 and 6 and fluid line apparatus of FIGS. 3, 4 and 8 will now be described with reference to FIG. 7.

The apparatus comprises a housing 50 mounting an anaesthetic vaporiser 51 for providing an anaesthetic. A flow meter 52 is connected via lines 53 to the vaporiser and line 54 to a manifold 55 and line 56 to an oxygen supply for mixing with the anaesthetic from the vaporiser 51. A line 57 from the manifold 55 and vaporiser 51 lead to a further flow meter 60 and an outlet for a line to the first conduit inlet 18. A three way switch 62 provides a further output 63 which may send anaesthetic gas to an induction chamber for treating subjects in the induction chamber (not shown).

Note that the invention is not limited to this anaesthetic machine arrangement and any anaesthetic machine arrangement may be used to provide anaesthetic fluid to the embodiments of the present invention.

A further embodiment of a fluid line apparatus in accordance with the present invention will now be described with reference to FIG. 8.

Figure 8:
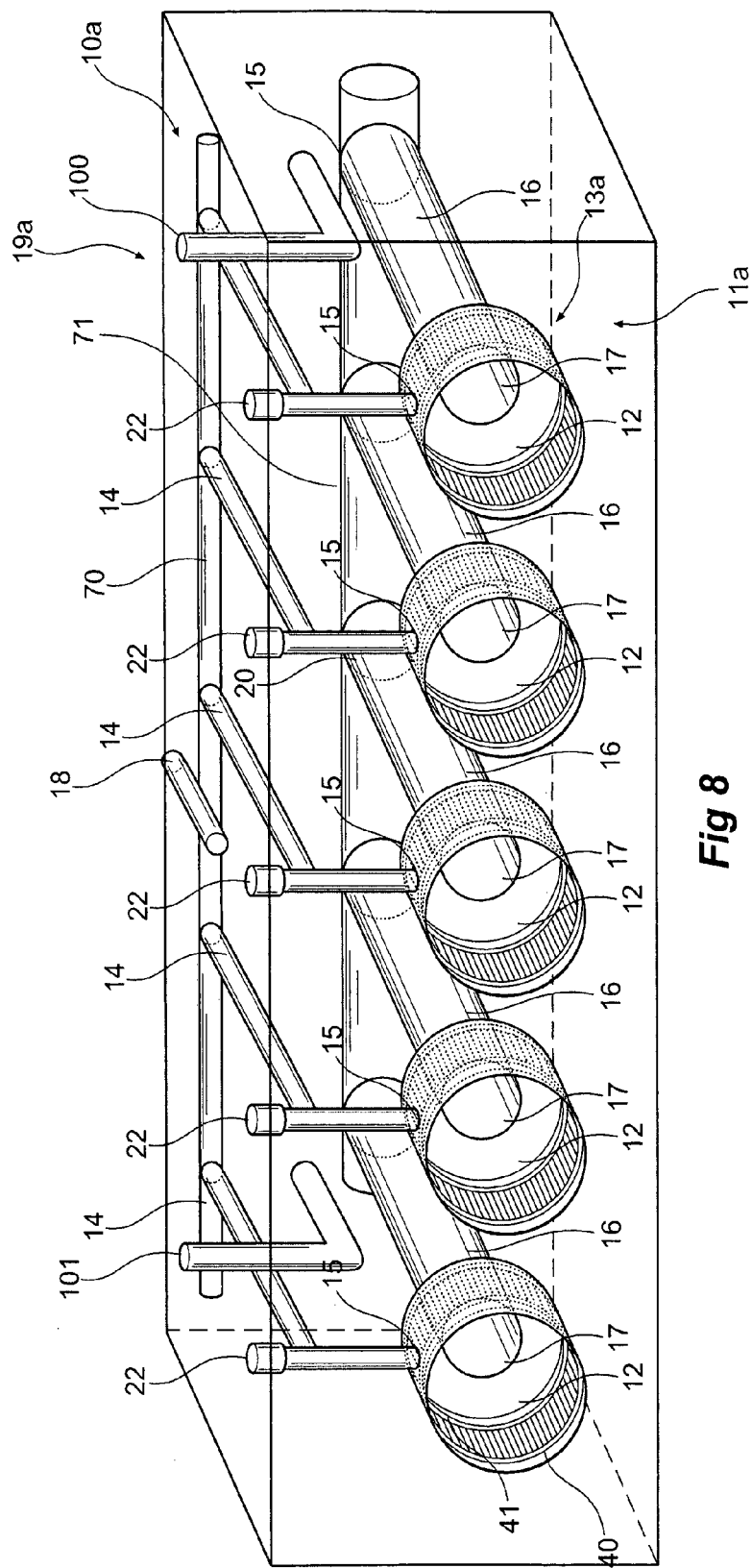

The fluid line apparatus of FIG. 8 comprises a fluid line substrate 10A, again in the form of a block substrate having conduits formed therein. The block 10A is essentially an integrated block of a plurality of fluid line substrates comprising respective first conduits 14, second conduits 16 and subject ports 12. The fluid lines have been given the same reference numerals as the fluid lines of FIGS. 3 and 4 and no further description will be given of these. Structure and operation is essentially the same as the embodiment of FIGS. 3 and 4, except in the fluid line substrate block 10A there are a plurality (in this case 5) of distinct fluid line substrates. This means that a plurality of subjects (in this case 5) can be treated at the same time. A plurality of masks (same as the mask apparatus of FIG. 5) may be utilised with the plurality of subject ports 12.

A surface 11A provides a support. Subject ports are formed in a front surface 13A adjacent the support 11A.

In this embodiment, the first conduits 14 are connected together in a manifold by a first common conduit 70 bored along the rear of the substrate 10A. The first common conduit 70 connects to the first conduit inlet 18. Only one first conduit inlet 18 is, therefore, necessary to serve the plurality of first conduits 14. This means that only a single line from, for example, an anesthetic machine (where the fluid is anesthetic) need be provided to provide anesthetic to the plurality of subjects.

The second conduits 16 are connected in a manifold arrangement by a second common conduit 71 running along the rear of the substrate 10A. The second conduit outlet 20 is connected to the second common conduit 71. Therefore only a single exhaust outlet 20 is required to serve the plurality of fluid lines. Therefore, only a single exhaust line an arrangement is required for exhausting and treating exhaust gas.

This embodiment therefore has the advantage that single anesthetic supply and exhaust lines may be provided to deal with a plurality of subjects. A plurality of very small animals may be treated at the same time, for example, using the manifolded arrangement. This advantageously greatly reduces the complexity required in the prior art for multiple gas lines. The block 10A also acts to stabilise the fluid lines and the subjects. Such an arrangement could be used in a chamber where imaging of the subjects is to be performed, where experiments need to take place on a number of subjects or other operations (e.g. tail bleeding of mice).

A single flowmeter 60 from an anesthetic machine such as described with reference to FIG. 7 may be used to provide an anesthetic to all the plurality of subjects using the fluid line apparatus of FIG. 8.

A plurality of adjustment mechanisms in the form of screws 22 are provided to enable adjustment of flow to each one of the plurality of subject ports 12. This enables flow to be regulated.

The use of a single flowmeter and single line to a plurality of ports greatly reduces the complexity of anesthetic machines as used in the prior art, where if they are to serve for a plurality of subjects they must have a requisite plurality of flowmeters and gas lines to those subjects.

Referring again to FIGS. 3 and 4, for subjects such as small animals or VSA's, the subjects will usually be placed on a supporting surface such as a bench. They may be placed directly on the bench, or on a support on the bench (e.g. a platform) or placed in some other orientation or subjects of different sizes may have to be catered for. To take account of this, the fluid line apparatus may be arranged so that the subject port 12 is at a different distance from the supporting surface depending upon the orientation of the substrate 10. Referring to FIG. 3, three different distances d1, d2 and d3 are provided by the subject port being off-set from the centre of the face 13. When the substrate is resting on surface 11, the distance from the supporting surface to the subject port 12 is d1. When resting on adjacent surfaces 11B or 11C, however, the subject port will be at different distances d2 and d3, respectively, from the supporting surface. This is a convenient way of dealing with the requirement to have subjects of different heights or sizes from the supporting surface.

In an embodiment of the present invention, further sensors may be provided proximate the subject ports 12 in order to monitor various parameters of the subject. For example, a pulse oximeter may be provided to monitor blood flow in the nose and mouth anatomy of the patient. The pulse oximeter may rely on radiation being passed across the white or otherwise translucent mask apparatus 30. The pulse oximeter may be placed in housing in the substrate 10 (10A not shown). Other sensors may include a thermister for measuring temperature.

Referring again to FIG. 8, a heating arrangement comprises a pair of heating conduits 100, 101 through which warm fluid (e.g. heated water) can be passed to heat the block 10A. Where the substrate is metal, it is conductive to heat, and therefore can be warmed to an appropriate temperature (e.g. 40° C.) to keep fluid in the conduits warm. Other heating arrangements may comprise electric circuits for warming the block 10A (e.g. electric heating elements). A similar heating arrangement may be provided in the block of the embodiment of FIGS. 3 and 4.

In an alternative embodiment, heating may be carried out by heating resistors placed in the conduits, or by heating resistors inter-integrated with the substrate. A mixture of fluid heating and electrical element heating may be implemented.

Sensors may be provided in the block to determine the temperature of the block.

In the embodiment of FIG. 8, the use of all the subject ports 12 at any one time may not be required. When not in use, a subject port may be plugged by a blind plug (not shown) to prevent delivery of fluid via the port.

The apparatus of FIGS. 3 to 8 may be used for treating small animals and very small animals in treatment chambers. For example the apparatus of FIG. 8 may be used to treat a number of mice or rats or other subjects in a treatment chamber.

The fluid line substrates in accordance with embodiments of the present invention may be used together to form a fluid line system useful in delivering anaesthetic to multiple subjects, such as (but not limited to) animals and very small animals (VSAs).

Figure 13:
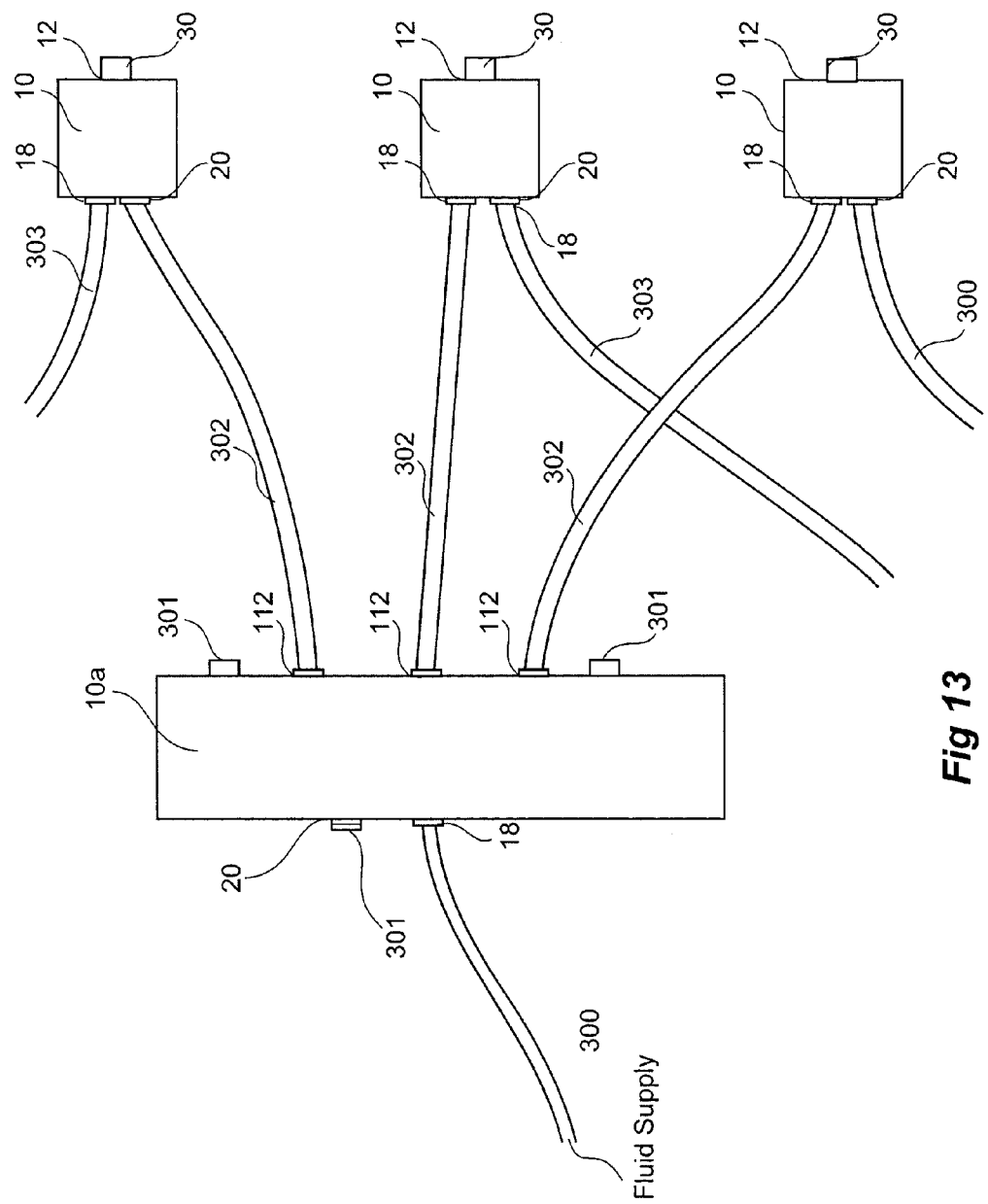
FIG. 13 is a schematic diagram of a system in accordance with an embodiment of the present invention, illustrating a plurality of fluid line substrates connected to deliver anaesthetic to a plurality of subjects.

FIG. 13 illustrates one potential arrangement for a system in accordance with an embodiment of the invention.

A multiple port block 10A, such as the embodiment of FIG. 8, for example, may be used in this embodiment of the system, as a "splitter" to provide an anaesthetic (or other fluid) supply to a plurality of single fluid inlet substrate blocks 10 (similar to the embodiment of FIGS. 3 and 4) at different work stations, for example.

In this embodiment, a fluid supply hose 300 supplies anaesthetic from an anaesthetic machine (not shown) to anaesthetic supply inlet 18 of the manifold 10A. The exhaust port 20 is sealed off with a plug 301. The anaesthetic is split and provided to ports 112 (there are three shown in use here), connected to further anaesthetic supply hoses 302. These separately supply anaesthetic to three respective fluid line substrates 10, via ports 18.

Via the subject ports 12 anaesthetic is then delivered to subjects (not shown) via a mask apparatus 30.

An advantage of this arrangement is that a single anaesthetic supply (eg single anaesthetic machine) may supply anaesthetic to a plurality of subjects who may be at work stations spaced from each other eg on different tables in a lab.

Remaining ports on the manifold 10A may be plugged (eg plugs 301).

Exhaust lines 303 may convey exhaust gas from the substrate outlets 20.

It will be appreciated that this system can be varied by using different numbers of ports on the intermediate manifold 10A to provide different numbers of single substrates 10. Further, there is even the option of using multiple manifolds 10A to supply many single substrates.

In labs and other places where anaesthetic gas is used, the anaesthetic gas, usually mixed with air or other exhaust gas, is generally exhausted into the atmosphere, after being passed out of the room via exhaust hoses and devices such as vacuum chambers or other suction type devices.

One of the issues with placing suction in an anaesthetic line, particularly with small humans and animals, is that it can cause great breathing difficulties if the suction pressure is too great. In fact, low or no suction pressures are required with very small animals, which can lead to difficulty in exhausting waste gases and pollution within the lab or other room where the anaesthesia is taking place.

FIGS. 14 through 16 illustrate a device in accordance with an embodiment of the present invention which ameliorates this problem. Exhaust hoses 350 from systems and fluid line substrates in accordance with the present invention are attached to ports 351 on a exhaust device 360 in accordance with an embodiment of the present invention.

Exhaust device 360 comprises a cylindrical housing (the cylinder may be of any cross-section) having outer walls 362 and an internal dividing wall 363. The internal dividing wall is open at the bottom, leaving a gap 364 for fluid flow. A suction outlet 365 is provided in a closure 366 at the top part of the device 360. The other side of the top part of the device 360 is open, opening 367.

In operation suction is applied to the outlet 365 via a hose 368. The amount of suction will depend upon the application but will be generally 20 to 60 milliliters mercury negative pressure.

This type of suction applied to anaesthetic circuits exhausts anaesthetising very small animals could be dangerous.

In this embodiment, however, the suction allows atmospheric air or other ambient gases to enter via the opening 367, and travel in a flow path as indicated by arrows 370.

This flow of atmospheric (or other ambient) gases passes by the ports 351 and entrains the exhaust gases from the exhaust lines 350. The amount of negative pressure applied to the exhaust ports 351 is therefore little or zero.

It will be appreciated that there may be variations on the embodiment of FIGS. 14 to 16, particularly there may be more or less than two exhaust ports, the device may be a different shape. Generally, any air break principle or device may be utilised.

The arrangement of FIGS. 14 to 16 or any variation on that arrangement may be used to facilitate exhaust of waste gases from embodiments of the invention described previously.

In the above embodiment, the fluid line substrate is a block in the form of a rectangular prism. The invention is not limited this. The substrate may be of any form. For example, the support may be a stand supporting the conduits which may be have been cast in metal rather than bored through a solid substrate (the metal walls of the cast are the substrate). Other materials and shapes may be used, e.g. plastics materials of different shapes. The substrate may be a block but may not be rectangular. It could be irregularly shaped, for example. There may be other variations.

The above embodiments are designed for small animals or very small animals. Although advantageous, the invention is not limited to this, and could be used with larger animals or human subjects.

In the above embodiment, the fluid delivered is an anesthetic gas mixture. The invention is not limited to this. Any fluid may be delivered using embodiments of the present invention, whether or not the fluid has a medical purpose.

In the apparatus of FIG. 8 described above, there are five subject ports. The invention is not limited to this. There may be more or less subject ports and fluid lines than this.

In the above embodiment, the mating arrangement mating the mask and subject port is plug and a socket arrangement. The invention is not limited to this, and other mating arrangements may be implemented to connect the mask to the subject port (e.g. a screw arrangement).

In the mask apparatus described above, the inlets are circumferentially placed about the mask. The invention is not limited to this. There may be one inlet only at one side of the mask or two inlets, each opposite each other. There may be any number of inlets.

In the above embodiment, the fluid line apparatus is used with a separate mask. The invention is not limited to this. A mask apparatus may be integrated with the fluid line apparatus e.g. formed with the subject port, for example. In another embodiment, no mask apparatus may be necessary and the subject's respiratory orifice may be placed directly in the subject port. A diaphragm may be placed directly over the entrance to the subject port.

A diaphragm may or may not be necessary. In some embodiments a diaphragm may not be needed.

Embodiments of the present invention allow for low flow, as opposed to the high flow open systems of the prior art. Active pumping of the anaesthetic gas mix is not required. There is little entrainment of environmental gas and little resistance to expiration of the subject.

Advantages of embodiments of the present invention, because of the low flow of gas, include a low fresh gas requirement (eg low anaesthetic usage); very low occupational pollution and very low environmental pollution.

Further, because of the low gas flow, the inspired gas can be heated (eg by way of heating the substrate blocks) in order to keep the animal warm. This can be particularly important with animals that are very small.

In the above embodiments, the fluid line apparatus implements the reduce re-breathing mechanism (conduit outlet being proximal with respect to the second conduit inlet in the subject port). The invention is not limited to this. The mask apparatus itself could implement the minimising re-breathing mechanism and the fluid line apparatus be of different structure. In some embodiments, a re-breathing mechanism may not be implemented at all. There would still be advantages in having a fluid line substrate in the form of embodiments of the present invention, without the minimal re-breathing feature and a separate mask arrangement (also without the minimal re-breathing feature), for example.

The term "comprising" (and its grammatical variations) as used herein are used in the inclusive sense of "having" or "including" and not in the sense of "consisting only of".

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The claims defining the invention are as follows:

1. An apparatus for facilitating delivery of a fluid to the respiratory tract of a subject, comprising:
    a fluid line substrate comprising a block of material having conduits formed therein for transmission of fluid,
    a support for stabilizing the substrate with respect to a supporting surface, and
    a subject port formed in the substrate opening outwardly of the block and arranged for delivery of fluid to a subject placed proximate the subject port,
    wherein the conduits formed in the fluid line substrate comprise a first conduit having a first conduit outlet which opens into the subject port, whereby fluid may be delivered to the subject port via the first conduit, and a second conduit having a second conduit inlet opening in the subject port, whereby fluid may flow from the subject port into the second conduit, the second conduit inlet being positioned distally within the subject port from the first conduit outlet whereby to induce a fluid flow to reduce rebreathing by the subject of fluid exhausted from the respiratory tract,
    wherein the support is a first surface of the block of material which is arranged to mount the block on a supporting surface and wherein the subject port is formed opening outwardly of a further surface of the block, the further surface being adjacent the first surface.

2. An apparatus in accordance with claim 1 further comprising a first conduit inlet formed in the fluid line substrate and arranged to receive input fluid, and a second conduit outlet formed in the fluid line substrate for exhausting output fluid.

3. An apparatus in accordance with claim 1, wherein the block of material is in the form of a rectangular prism, and the first surface is one or more of the surfaces of the rectangular prism which are contiguous with the further surface.

4. An apparatus in accordance with claim 3, wherein the first conduit inlet and the second conduit outlet are formed in a surface of the block opposite to the further surface.

5. An apparatus in accordance with claim 1, wherein the subject port is positioned in the substrate such that for a plurality of different orientations of the substrate block with respect to the supporting surface the subject port is positioned at respective different distances from the supporting surface.

6. An apparatus in accordance with claim 1, further comprising a mating arrangement for mating the subject port with a mask apparatus, the mask apparatus comprising an enclosure having a first opening arranged to fit over a respiratory opening of the subject, and at least one second opening arranged to receive fluid provided to the subject port from the first conduit outlet.

7. An apparatus in accordance with claim 6, wherein the mating arrangement comprises a socket portion of the subject port arranged to receive a plug portion of the enclosure.

8. An apparatus in accordance with claim 6, wherein the mask apparatus comprises a third opening and the second conduit inlet is arranged to communicate with the third opening to receive a flow of fluid from the third opening into the second conduit.

9. An apparatus in accordance with claim 1, further comprising an adjustment mechanism arranged to enable adjustment of fluid flow to the first conduit outlet.

10. An apparatus in accordance with claim 9, wherein the adjustment mechanism comprises an adjustable plug arranged to project within the first conduit by a variable amount.

11. An apparatus in accordance with claim 1, comprising a plurality of fluid line substrates comprising a respective plurality of first conduits, second conduits and subject ports for facilitating delivery of fluid to a respective plurality of subjects placed proximate the respective subject ports.

12. An apparatus in accordance with claim 11, wherein the plurality of fluid line substrates are integrated as a single combined fluid line substrate.

13. An apparatus in accordance with claim 12, wherein the combined fluid line substrate is in the form of a manifold, wherein each of the respective plurality of first conduits are connected at ends distal from the plurality of subject ports to a first common conduit, the first common conduit opening into a first conduit inlet for receiving input fluid.

14. An apparatus in accordance with claim 13, wherein the respective plurality of second conduits are connected at ends distal from the subject port to a second common conduit, the second common conduit opening into a second conduit outlet for exhausting output fluid.

15. An apparatus in accordance with claim 1, further comprising a heating arrangement for heating the fluid line substrate.

16. An apparatus in accordance with claim 15, wherein the heating arrangement comprises at least one heating conduit formed in the substrate and arranged to receive heated fluid.

17. Apparatus in accordance with claim 1, the apparatus being dimensioned so that it is arranged to provide fluids to the respiratory tracts of Very Small Animals (VSA).

18. An apparatus in accordance with claim 17, being dimensioned to be suitable for VSAs of 500 grams or less.

19. An apparatus in accordance with claim 1, wherein the fluid is an anaesthetic gas mix.

20. An apparatus for facilitating delivery of fluid to the respiratory tract of a subject, comprising:
a fluid line substrate ha ng conduits formed therein for transmission of fluid,
a support for stabilizing the substrate with respect to a supporting surface, and
a subject port formed in the substrate opening outwardly of the substrate and arranged for delivery of fluid to a subject placed proximate the subject port,
wherein the conduits formed in the fluid line substrate comprise a first conduit having a first conduit outlet which opens into the subject port, whereby fluid may be delivered to the subject port via the first conduit, and a mating arrangement for mating the subject port with a mask apparatus, the mask apparatus comprising an enclosure having a first opening arranged to fit over a respiratory opening of the subject and at least one second opening arranged to receive fluid provided to the subject port from the first conduit outlet, and
wherein the mating arrangement comprises a plug portion of the enclosure Which is arranged to fit within the subject port.

21. A mask apparatus for facilitating delivery of fluid to the respiratory tract of a subject, the mask apparatus comprising,
an enclosure having a first portion arranged to fit over a respiratory opening of the subject to deliver fluid to the respiratory opening of the subject,
a mating arrangement arranged to mate with a fluid line apparatus comprising a fluid line substrate comprising a first conduit formed therein for transmission of fluid,
a subject port formed in the substrate, wherein the first conduit has a first conduit outlet which opens into the subject port, and
an inlet arranged to communicate with the first conduit outlet when the mask apparatus is mated with the fluid line apparatus, whereby fluid may be delivered to the subject via the first conduit outlet and the first portion of the mask,
wherein the mating arrangement comprises a plug portion of the enclosure which is arranged to fit within the subject port of the fluid line substrate.

22. A mask apparatus in accordance with claim 21 further comprising an outlet from the enclosure, the outlet being positioned distally with respect to the inlet, whereby to induce a fluid flow to reduce re-breathing of fluid exhausted from the respiratory tract of the subject.

23. A mask apparatus in accordance with claim 21, the mask enclosure being of a size appropriate to suit a Very Small Animal (VSA) as the subject.

24. A mask apparatus in accordance with claim 23, wherein the mask enclosure is of a length less than 100 mm, and an opening of the first portion within which a respiratory opening of the VSA is to fit is 50 mm or less in width.

25. A mask apparatus in accordance with claim 24, wherein the width of the opening is 25 mm or less.

26. A mask apparatus in accordance with claim 21, wherein the first portion is offset axially with respect to the plug portion, whereby to receive the respiratory opening anatomy of a subject offset from the subject port.

27. A mask apparatus in accordance with claim 21, wherein the mask enclosure has a substantially cylindrical transverse cross section, and wherein the inlet is arranged such that fluid is introduced into the enclosure at east at opposite sides of the cylinder.

28. A mask apparatus in accordance with claim 27, wherein the inlet comprises a plurality of orifices in the enclosure positioned about the periphery of the cylindrical cross section.

29. A mask apparatus in accordance with claim 21, further comprising a diaphragm arranged to fit over an opening in the first portion, the diaphragm having a diaphragm opening to receive the respiratory opening of the subject.

30. A mask apparatus in accordance with claim 29, wherein the diaphragm is arranged to receive the nose and mouth of the subject through the diaphragm opening and the periphery of the hole abuts the nose and mouth anatomy of the subject.

31. A mask apparatus in accordance with claim 21, herein the fluid is an anaesthetic gas mix.

32. A mask apparatus in accordance with claim 21, wherein the fluid line apparatus is the apparatus of claim 1.

* * * * *